United States Patent
Peng et al.

(10) Patent No.: US 6,799,730 B2
(45) Date of Patent: Oct. 5, 2004

(54) ULTRASONIC FOG MAKER AND METHODS OF DRUG DELIVERY AND AIR FRESHENING

(75) Inventors: Kuang Peng, Hampton, VA (US); Zuoxin Wu, Guang Dong (CN); Deming Hu, Guang Dong (CN); Weitao Deng, Guang Dong (CN)

(73) Assignee: Palantic Trading, Yorktown, VA (US)

( * ) Notice: Subject to any disclaimer, the term of this patent is extended or adjusted under 35 U.S.C. 154(b) by 0 days.

(21) Appl. No.: 10/295,023

(22) Filed: Nov. 15, 2002

(65) Prior Publication Data

US 2003/0094508 A1 May 22, 2003

(51) Int. Cl.⁷ .............................. B05B 1/08; B05B 3/04; B05B 17/04
(52) U.S. Cl. .......................... 239/102.2; 239/4; 261/81
(58) Field of Search .......................... 239/102.1, 102.2, 239/211, 4; 261/81

(56) References Cited

U.S. PATENT DOCUMENTS

| | | | |
|---|---|---|---|
| 3,069,794 A | * | 12/1962 | Stalcup ........................ 40/407 |
| 3,901,443 A | * | 8/1975 | Mitsui et al. ............. 239/102.2 |
| 4,752,422 A | * | 6/1988 | Uchida et al. ................. 261/81 |
| 5,011,632 A | * | 4/1991 | Yano et al. .................... 261/81 |
| 5,030,253 A | * | 7/1991 | Tokuhiro et al. .............. 95/216 |
| 5,610,668 A | | 3/1997 | Mage |
| 5,729,863 A | | 3/1998 | Papesh |
| 5,893,515 A | | 4/1999 | Hahn et al. |
| 5,906,202 A | | 5/1999 | Schuster et al. |
| 5,934,272 A | | 8/1999 | Lloyd et al. |
| 5,989,128 A | * | 11/1999 | Baker et al. ................... 472/65 |
| 6,009,645 A | | 1/2000 | Shimizu et al. |
| 6,296,196 B1 | * | 10/2001 | Denen et al. ................... 239/4 |
| 6,361,024 B1 | | 3/2002 | Carson |
| 6,375,090 B1 | * | 4/2002 | Beidokhti ..................... 239/17 |
| 6,379,633 B1 | | 4/2002 | Garlick |

* cited by examiner

Primary Examiner—William C. Doerrler
(74) Attorney, Agent, or Firm—Foley & Lardner LLP

(57) ABSTRACT

An ultrasonic fog generator creates a fog of a liquid such as water. The visual appearance of the fog may be altered such as by being illuminated by one or more lights having one or more colors. Further, the fog may be used to deliver pharmaceuticals to one or both of the lungs of a patient.

17 Claims, 6 Drawing Sheets

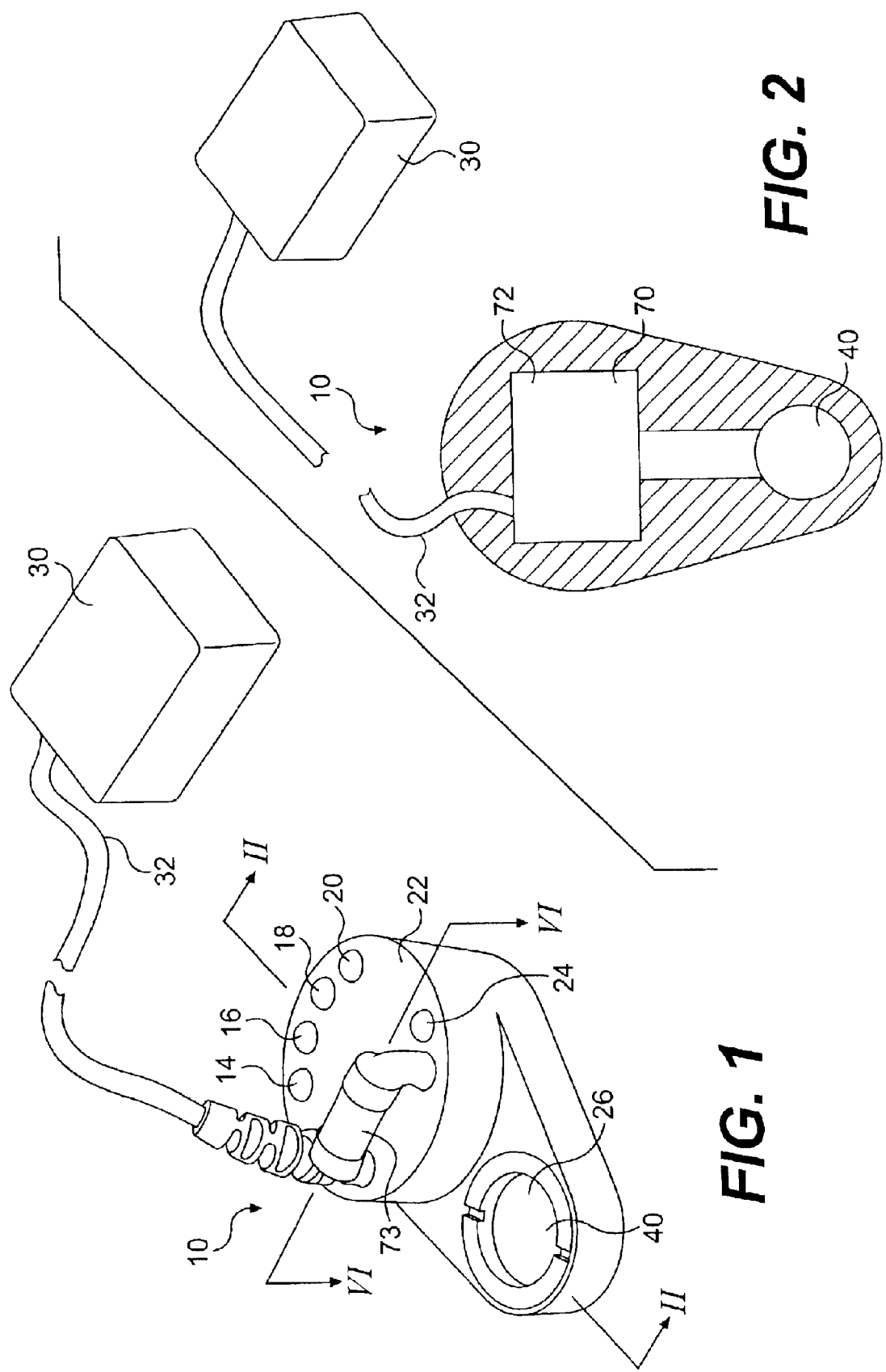

ULTRASONIC FOG MAKER AND METHODS OF DRUG DELIVERY AND AIR FRESHENING

CROSS-REFERENCE TO RELATED APPLICATIONS

This application claims priority to Chinese Design Patent Application Serial Nos. ZL 01-3-53634.6 (Certificate No. 255801), ZL 01-3-53635.4 (Certificate No. 253978), and ZL 01-2-58009.0 (Certificate No. 515796), all of which were filed on Nov. 16, 2001.

BACKGROUND OF THE INVENTION

1. Field of the Invention

The present invention relates to creating fog, which may be in the form of mist. More particularly, the invention relates to using fog or mist in a visually appealing display or as a conduit for drug delivery.

2. Description of the Related Art

There are generally four types of visual vapor or fog generators on the market today. Carbon dioxide ("$CO_2$") fog generators generate a visual fog using a solid block of $CO_2$ (i.e., dry ice) which is dropped into a bath of deionized ("DI") water heated to 140° F. or higher. One disadvantage of $CO_2$ fog generators is that the fog quantity they produce is unregulated, i.e., the fog quantity cannot be readily applied in any situation without adjusting the size of the of $CO_2$ block as the quantity of fog produced is largely based on the size of the block used. Further, in applications requiring a large amount of fog, the size of the $CO_2$ fog generator can become large and cumbersome. In addition, as the $CO_2$ block melts, the quantity of fog output from the fog generator diminishes and the temperature of the DI bath is lowered which, in time, will require a reheating of the water or adding more hot water thereto. Further, when the $CO_2$ block melts, it must be replaced by another costly $CO_2$ block.

Helium bubble generators, as the name implies, generate small helium filled bubbles of water that float in the air at almost neutral buoyancy. Unfortunately, helium bubble generators tend to produce a small quantity of bubbles that may fail to create a dense and realistic fog. Further, increasing the helium levels in a room may have a negative impact on the comfort of people in the room.

A third type of fog generator generates a fog by passing steam from boiling water through a bath of liquid nitrogen ("$N_2$") creating a super cooled fog. Similar to the $CO_2$ block fog generator, liquid $N_2$ fog generators tend to be large and require a continuous supply of costly of liquid $N_2$. Further, these fog generators may be hazardous because they require both a boiler to heat the water and extremely cold liquid $N_2$ to operate.

Finally, ultrasonic fog generators create fog by vibrating a bath of water using ultrasonic sound. The fog may be disbursed through a long hose in which water vapor fog may condense.

One common fact among the aforementioned fog generators is the creation of fog in a way that fails to be visually pleasing, i.e., the only thing created is fog. In addition, the fog created serves no purpose other than perhaps being indicative of airflow and simulating fog.

SUMMARY OF THE INVENTION

The invention herein contains multiple embodiments including a housing for an ultrasonic fog generator. In this embodiment, the housing includes a transducer and a visually appealing display. The transducer is adapted to vibrate ultrasonically. When the housing is positioned in a source comprising a liquid and when the transducer vibrates ultrasonically, the housing is adapted to create a fog from the liquid in the source; the fog emanates from the liquid source. The visually appealing display is adapted to alter an appearance of the fog.

In a further embodiment of the housing, the housing may be adapted to be hand-held.

In another further embodiments of the housing, the liquid may be water.

In another further embodiment of the housing, the fog may be in the form of a mist.

In other further embodiments of the housing, the housing may addition include a sensor. Further, the sensor may be adapted to monitor a property of the liquid contacting the housing. In addition, a current control system may be adapted to stop vibration of the transducer in response to the monitored property.

In other further embodiments of the housing, the visually appealing display may include at least one light. Further, the visually appealing display may include at least two lights, wherein the lights are adapted to radiate light of at least two different colors. In addition, the colors which the lights are adapted to radiate may be variable.

In another further embodiment of the housing, the visually appealing display may include at least two lights, wherein the lights are adapted to radiate light of at least two different colors. In addition, the visual display may also include a light diffuser through which the at least two colors of light may pass.

In other further embodiments of the housing, the visually appealing display may include at least one light and a stand adapted to support the housing. Further, the stand may maintain the housing and the liquid source above a surface such that the fog may fall toward the surface after emanating from the liquid source.

In another further embodiment of the housing, the transducer may be adapted to vibrate between about 1.6 MHz and about 1.8 MHz. Further, the transducer may be adapted to vibrate at about 1.7 MHz.

In another further embodiment of the housing, the liquid may include a fragrance that is dispersed in the fog.

The invention also contemplates a method for delivering at least one pharmaceutical to at least one lung of a patient. This method includes: (a) providing a source comprising the at least one pharmaceutical, wherein each of the at least one pharmaceutical is in a substantially liquid form; (b) positioning a transducer in the source comprising the at least one pharmaceutical; (c) vibrating ultrasonically the at least one pharmaceutical with the transducer, to create a fog of the at least one pharmaceutical; (d) inhaling the fog formed of the at least one pharmaceutical, wherein the inhaling is done by the patient; and (e) delivering the fog to the at least one lung of the patient.

In a further embodiment of the method, the step of inhaling the fog may include: (d)(1) passing the fog through an outlet of a housing which contains the source comprising the transducer and the at least one pharmaceutical; and (d)(2) delivering the fog to the mouth of the patient through a conduit connected to the outlet.

In another further embodiment of the method, the method may further include: (f) monitoring a property of the at least one pharmaceutical with a sensor.

In another further embodiment of the method, the method may further include: (f) monitoring a property of the at least one pharmaceutical with a sensor; and (g) stopping the vibrating of the transducer if property of the at least one pharmaceutical, as measured by the sensor, is outside a predetermined range for the property.

In another further embodiment of the method, the step of vibrating ultrasonically the at least one pharmaceutical with the transducer may include: vibrating the transducer at between about 1.6 MHz and about 1.8 MHz, such as for example, at about 1.7 MHz.

The invention also contemplates a method for adding at least one fragrance to ambient air in a room. This method includes: (a) providing a source comprising the at least one fragrance, wherein each of the at least one fragrance is in a substantially liquid form; (b) positioning a transducer in the source comprising the at least one fragrance; (c) vibrating ultrasonically the at least one fragrance with the transducer, to create a fog of the at least one fragrance; and (d) emanating the fog formed of the at least one fragrance into the ambient air.

In a further embodiment of the method of adding fragrance to the ambient air in a room, the fragrance may be dissolved in a liquid solvent.

In another further embodiment of the method of adding fragrance to the ambient air in a room, the fragrance may be dissolved in a liquid solvent. Further, the method may also include: (e) monitoring a property of the at least one fragrance and the liquid solvent in the source with a sensor.

In another further embodiment of the method of adding fragrance to the ambient air in a room, the fragrance may be dissolved in a liquid solvent. Further, the method may also include: (e) monitoring a property of the at least one fragrance and the liquid solvent in the source with a sensor.; and (f) stopping the vibrating of the transducer if property of the at least one fragrance and the liquid solved in the source, as measured by the sensor, is outside a predetermined range for the property.

In another further embodiment of the method of adding fragrance to the ambient air in a room, the step of vibrating ultrasonically the at least one fragrance with the transducer may include: vibrating the transducer at between about 1.6 MHz and about 1.8 MHz, such as for example, at about 1.7 MHz.

The invention also contemplates a device for ultrasonically generating a fog of at least one liquid pharmaceutical. The device includes a transducer and a source containing the at least one liquid pharmaceutical. The transducer is adapted to vibrate ultrasonically and is positioned in the at least one liquid pharmaceutical. When the transducer vibrates ultrasonically, at least a portion of the at least one liquid pharmaceutical is changed into a fog which emanates from the device.

In a further embodiment of the device, the device may be adapted to be hand-held.

In another further embodiment of the device, the fog may emanate from the device through an outlet.

In another further embodiment of the device, the fog may emanate from the device through an outlet and into a conduit connected to the outlet. Further, the conduit may be adapted to transport the fog to a mouth of a patient.

In another further embodiment of the device, an air inlet may be provided in the device to prevent a vacuum from developing in the device if the pressure at the outlet is greatly reduced.

In another further embodiment of the device, the fog may emanate from the device through an outlet and into a conduit connected to the outlet. Further, the conduit may be adapted to transport the fog to a mouth of a patient and the conduit may be formed a material selected from the group consisting of rubber and plastic.

In another further embodiment of the device, the at least one pharmaceutical may be adapted to treat a condition of a lung.

In another further embodiment of the device, the at least one pharmaceutical may be adapted to treat asthma.

In another further embodiment of the device, the transducer may be adapted to vibrate at between about 1.6 MHz and about 1.8 MHz, such as, for example, at about 1.7 MHz.

These and other features, aspects, and advantages of the present invention will become more apparent from the following description, appended claims, and accompanying exemplary embodiments shown in the drawings.

BRIEF DESCRIPTION OF THE DRAWINGS

The accompanying drawings, which are incorporated in and constitute a part of the specification, illustrate an embodiment of the invention and together with the description, serve to explain the principles of the invention.

FIG. 1 is a perspective view of a housing for an ultrasonic fog generator, the housing having a plurality of lights thereon;

FIG. 2 is a cross-sectional view of the housing of FIG. 1 showing an ultrasonic transducer, a current control system interposed between a power source and the transducer, the cross-section being taken along line II—II in FIG. 1;

DETAILED DESCRIPTION

Figure 3:
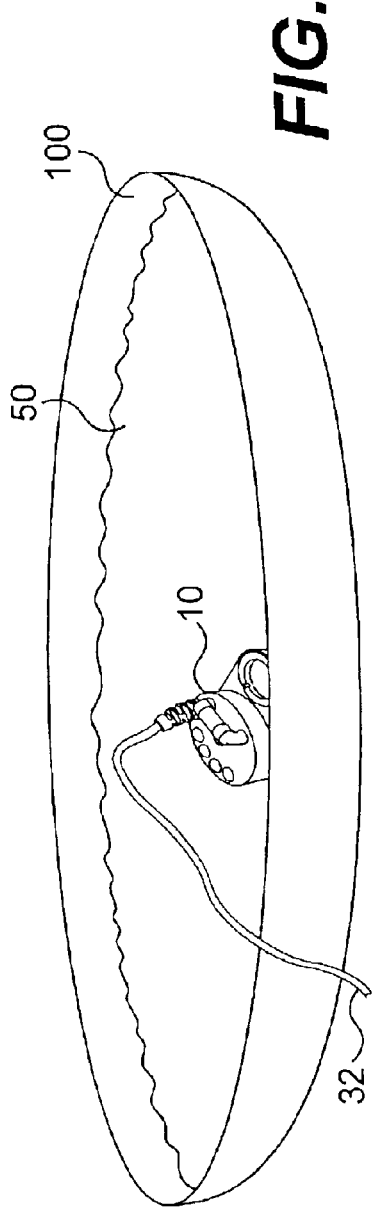
FIG. 3 is a perspective view of the housing of FIG. 1 in a container of liquid.

Reference will now be made in detail to presently preferred embodiments of the invention, which are illustrated in the drawings. An effort has been made to use the same reference numbers throughout the drawings to refer to the same or like parts.

FIG. 1 is a perspective view of a housing 10 for an ultrasonic fog generator. The housing 10, which is preferably sized to be hand-held, has a plurality of lights 14, 16, 18, 20 thereon. Each of the lights 14, 16, 18, 20 is adapted to emit a particular color of light which may be the same as or different than the color emitted by one or more of the other lights 14, 16, 18, 20. In addition, each of the lights 14, 16, 18, 20 may be adapted to change colors during use, i.e., the colors may be variable. Power for the lights 14, 16, 18, 20 is provided by a power source 30 and is delivered to the housing by a power cord 32, as later described in detail.

Also shown on a top side 22 of the housing 10 is an indicator lamp 24, an ultrasound depression 26 housing a transducer 40, and a sensor 73 of a current control system 70 (later described in detail). The indicator lamp 24 contains a light source, such as a light emitted diode ("LED"), a halogen bulb, etc., which will continuously radiate light when the housing 10 is connected to a power source 30. It should be readily apparent that the power source 30 may be any conventional power source such as a wall outlet proving AC current or a DC battery; the type of power source 30 employed will, however, determine whether an AC/DC converter is necessary. Regardless, power entering the housing 10 should be DC voltage, preferably at about 24 V. Accordingly, if an AC power source is used, a transformer would be necessary.

As previously mentioned, the ultrasound depression 26 houses a transducer 40 contained within the housing 10. The transducer 40 may be a ceramic material which is adapted to vibrate at ultrasonic rates and which is electrically connected to the power source 30; the ceramic material can change electrical oscillations into mechanical oscillations (i.e., the ceramic material may vibrate at ultrasonic rates). It is within the ultrasound depression 26 that a conductive or at least semiconductive liquid 50 will be converted to a fog 60, which may be in the form of a mist, depending on the size of the droplets released into the air. The liquid 50 may be water, a pharmaceutical, a fragrance, a combination of any of these, or other liquid. Preferably, the housing 10 will be submerged between about 1.0" and about 2.0" and preferably at about 1.5" in the liquid 50.

The liquid 50 within the ultrasound depression 26 is oscillated by the transducer 40 within the housing 10 at between about 1.6 MHz and about 1.8 MHz and preferably at about 1.7 MHz. A variety of ultrasonic transducers manufactured by Nanhai Gentle Electronic Company, Ltd. (China) are capable of producing these oscillations; one preferable model is sold under product no. DH-24B. Another capable transducer is described in U.S. Pat. No. 6,361,024. One transducer 40 capable of producing such oscillations is shown in FIG. 2 which is a cross-sectional view of the housing of FIG. 1 taken along line II—II therein. As shown in FIG. 2, in addition to the ultrasonic transducer 40, the housing 10 also contains a current control system 70 (later described in detail).

As shown in FIG. 2, power is delivered to the transducer 40 from the source 30 via a power cord 32 and through the current control system 70. If the volume of the liquid 50 above the housing 10 (as measured by the current control system 70 and as later described in detail) is below a predefined limit, the current control system 70 may limit the amount of current from the power source 30 supplied to the transducer 40. At a later time when the volume of the liquid 50 above the housing 10 is at or above the predefined limit, the current control system 70 can increase the current to the transducer 40 thereby enabling the transducer 40 to oscillate, preferably ultrasonically.

Absent a current control system 70, if the housing 10 were insufficiently submersed, the transducer 40 may oscillate the liquid near the surface to such a degree that liquid, rather than fog, may be ejected from the container 100. Further, all of the liquid 50 on top of the housing 10 could be ejected from the container 100, thereby causing the housing 10 to operate without any liquid thereon and, therefore, wasting power and possibly damaging the device (e.g., overheating the ceramic transducer 40). Accordingly, to prevent this situation, a current control system 70 may be used to prevent power from reaching the transducer 40 when the housing 10 is insufficient submerged (or not submerged) in a liquid 50.

Figure 6:
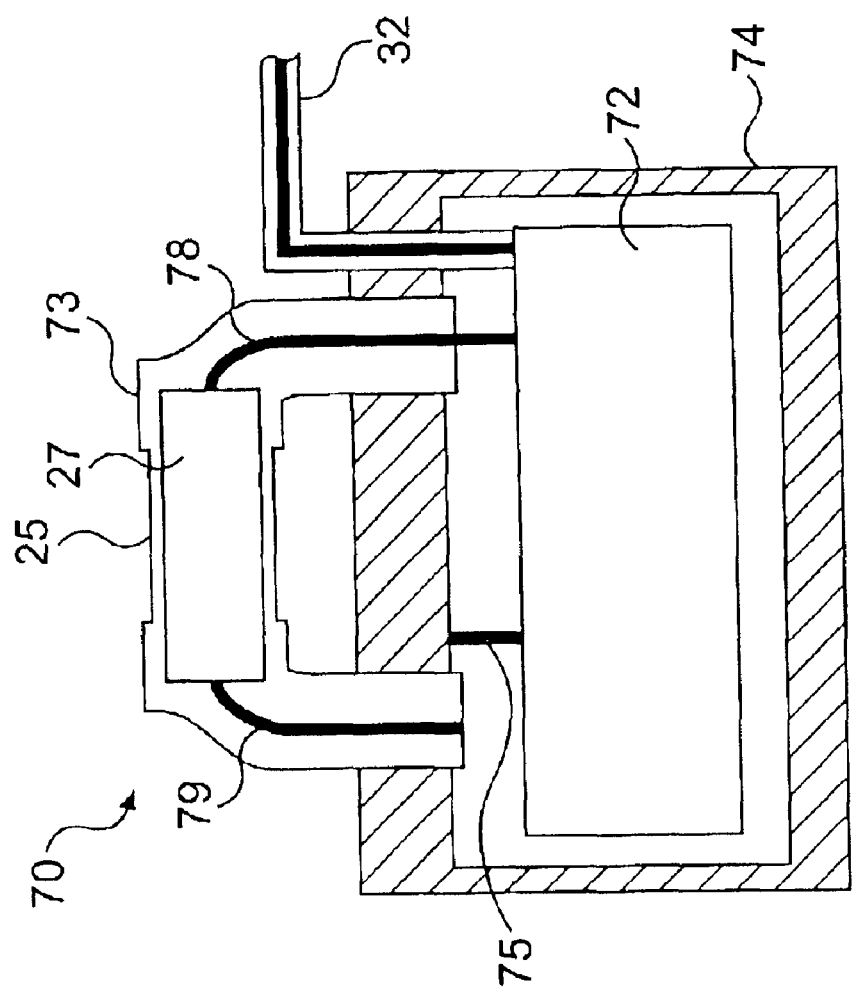
FIG. 6 is a cross-sectional view of the housing of FIG. 1, the cross-section being taken along live VI—VI in FIG. 1.
Figure 7:
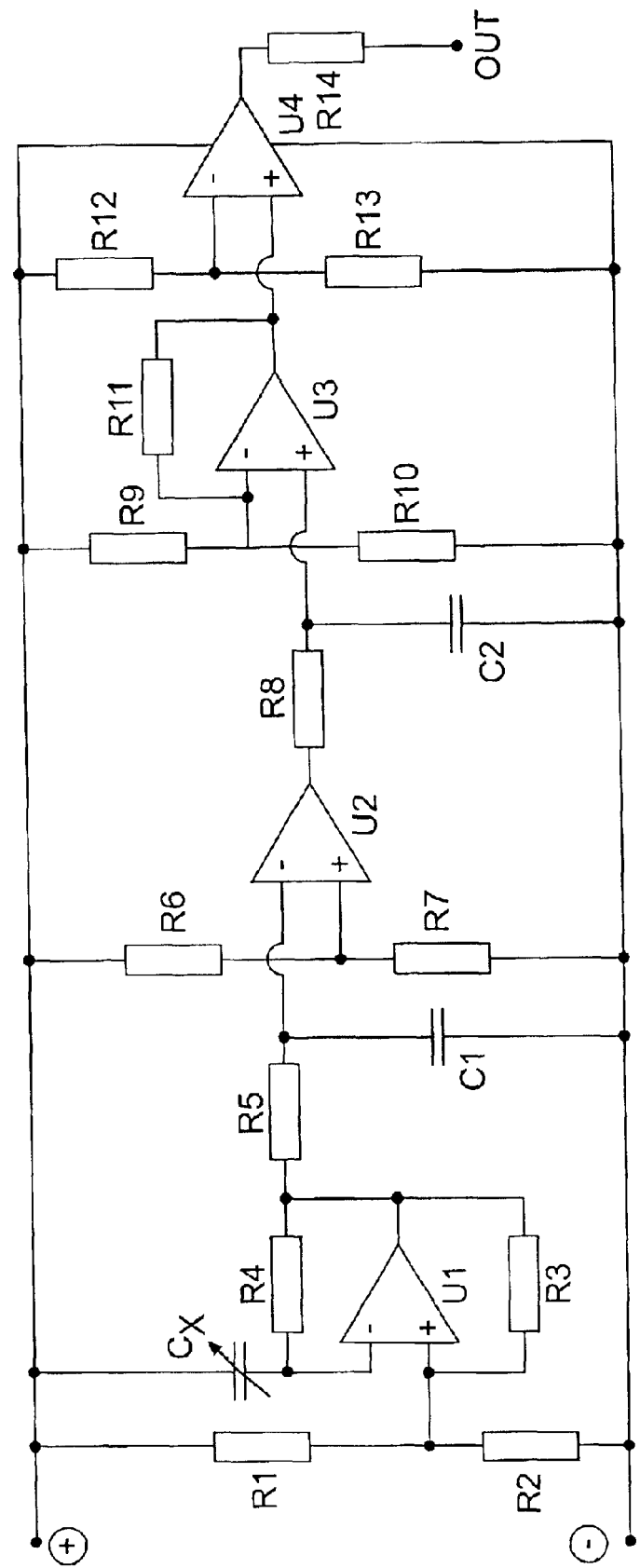
FIG. 7 is a circuit diagram representing theoretically the function of the current control system.

The current control system 70, which is described in detail in Chinese Patent Document No. ZL 96,236,955.1 and which is incorporated herein by reference, will now be explained in detail with respect to FIGS. 6 and 7. As shown in FIG. 6 (which is a cross-sectional view of the housing of FIG. 1 taken along live VI—VI thereof), there is provided a circuit board 72 which, in conjunction with the current control system 70, controls whether power travels from the power source 30 to the transducer 40.

Connected electrically to the circuit board 72 is a first conductor 78 (which may be a wire) which, in turn, is connected to a volume sensor 73. The sensor 73, which projects out of the housing 10, includes an insulation wrapping 25 and contains a material 27 which has a variable resistance, the material 27 preferably being copper. For example, the resistance of the material could change in response to the temperature of the liquid 50 therearound, the temperature presumably being lower in a bottom portion of the container 100 holding the liquid 50 than in an upper portion thereof. For instance, a change in resistance based on a change is temperature is governed by the following equation:

$$R_T = R_0[1 + \alpha(T - T_0)],$$

where $R_T$ is the resistance at temperature "T", $R_0$ is the resistance at a reference temperature "$T_0$", and $\alpha$ is a coefficient of resistivity for a given material. By way of another example, the resistance of the material 27 could vary with the pressure applied thereto by the liquid 50, the pressure being greater in a bottom portion of the container 100 than in an upper portion thereof. Such a change in resistance could be affected by a pressure sensitive resistor. However, the invention is not limited to any particular property which may alter the resistance of the material 27.

As the sensor 73 is lowered in a liquid 50 (i.e., as the depth of submersion increases), the resistance of the material 27 correspondingly increases. As a result, as the depth of the sensor 73 increases, the voltage across the sensor 73 will increase, provided current remains substantially constant. In addition, the portion of the wrapper 25 on the exterior of the sensor 73 which passes through the upper side 22 of the housing 10 may be sealed with laminate plastic and/or rosin glue.

On an opposite end of the sensor 73 there is provided a second conductor 79. When the housing 10 is immersed in a liquid 50 and the resistance of the material 27 increases, the voltage at the second conductor 79 increases. As the second conductor 79 is insulated by the wrapping 25, the wrapping 25 acts as a dielectric between the second conductor 79 and the liquid 50, i.e., the second conductor 79 and the liquid 50 form a capacitor. As the voltage experienced by the second conductor 79 increases, the capacitance between the second conductor 79 and the liquid 50 (represented by $C_X$ in FIG. 7) will also increase.

As a result of the capacitance between the second conductor 79 and the liquid 50, current will flow in the liquid 50 (i.e., the other "plate" of the capacitor) and will pass through the conductive outer casing 74 (e.g., which may be formed from a metallic material such as, for example, chrome or copper) and back into the circuit board 72 via a third conductor 75, with a variable voltage. When the voltage at the third conductor reaches a predetermined level, a comparator (represented by U2 in FIG. 7) will act to direct the current to the transducer 40 thereby enabling it to oscillate, preferably ultrasonically.

It should be noted that as the power through housing is DC current/voltage, there is no substantial risk of electrical shock from the current in the liquid 50. In light of the aforementioned, the depth of the water affects the sensor 73 and the voltage thereacross such that it acts as a switch. It should also be noted that as the sensor 73 is insulated (by the insulation wrapping 25) from the liquid 50, oxidation of the sensor 73 will be substantially inhibited.

FIG. 3 is a perspective view of the housing 10 of FIG. 1 in a container 100 of liquid 50. As previously mentioned, the liquid 50 may be water, a pharmaceutical, a fragrance, a combination of any of these, or other liquid. Preferably, the liquid 50 is water. The housing 10 is placed in the container 100 such that it is submersed in the liquid 50 (other than the power cord 32 which may not be submersed). The housing 10 is submersed to a depth such that the transducer 40 will cause the liquid near the surface of the liquid 50 to oscillate. As the liquid 50 near the surface oscillates, it will evaporate in the form of a visual fog or mist. The density of the fog or mist will depend on the depth at which the housing 10 is submersed in the liquid 50.

Figure 4:
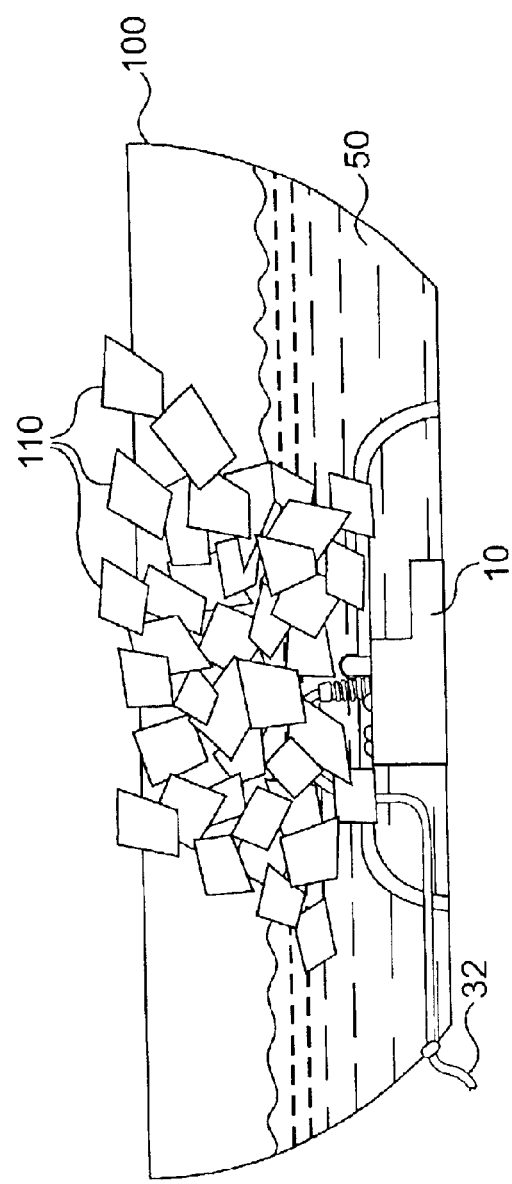
FIG. 4 is a cross-sectional view of a container of having a light diffuser in the form of faux ice therein, the ice covering a housing of the type shown in FIG. 1.

In conjunction with the container 100, the housing 10 (and the lights 14, 16, 18, 20) can be incorporated into a visually appealing display. For example, as shown in FIG. 4 a light diffuser 110 (such as a pile of faux ice) may be added to the container 100 to cover the housing 10 substantially. The light diffuser 110 may be formed of plastic, quartz, a clear polymer, or other clear generally solid material which will not dissolved in the liquid 50. Further, preferably, the light diffuser 110 will not chemically react or interact with the liquid 50. In this embodiment, the light emitted by the lights 14, 16, 18, 20 will radiate through the light diffuser 110, thereby illuminating the light diffuser 110.

Figure 5:
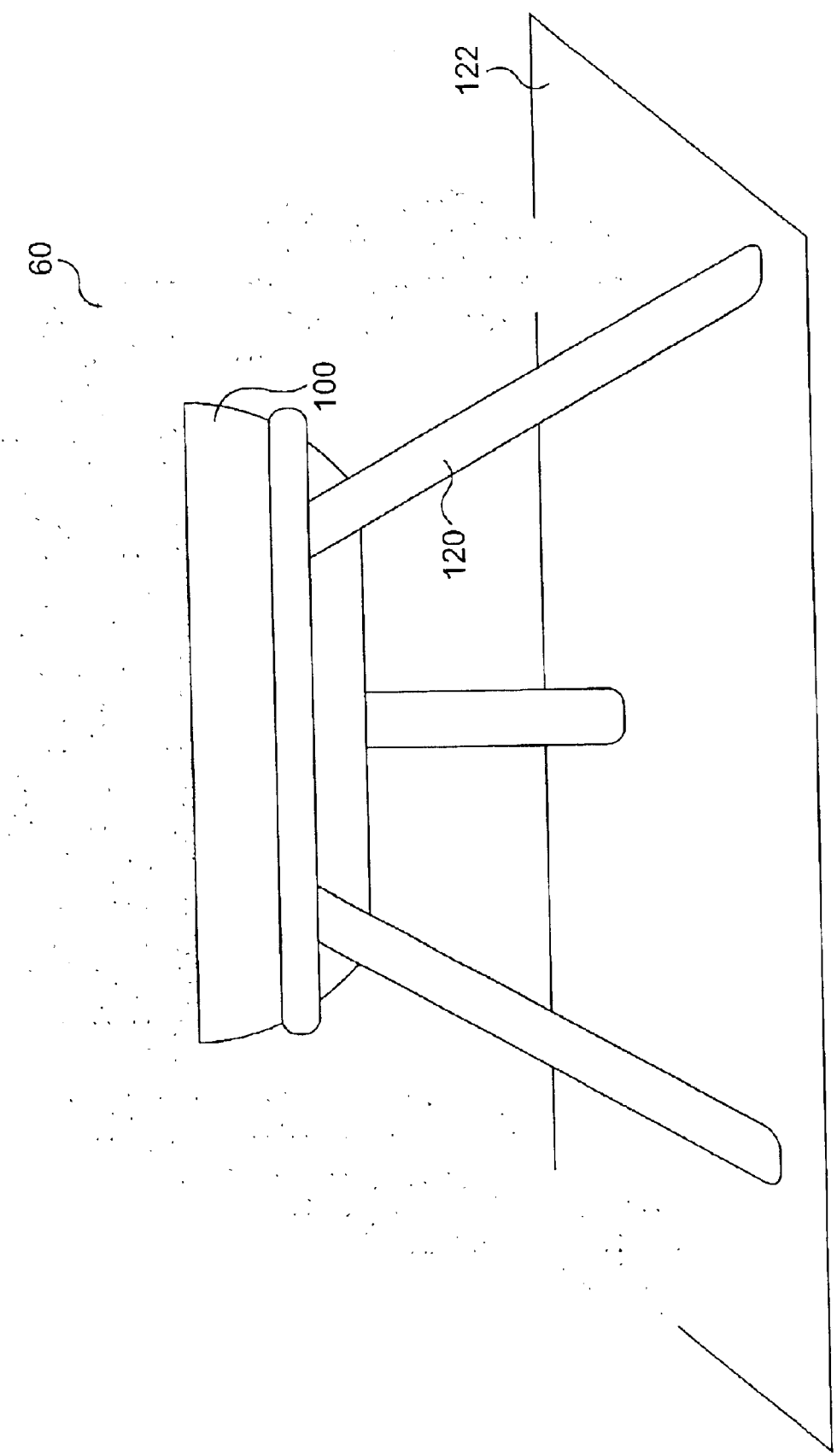
FIG. 5 is a side view of the housing and container of FIG. 3 supported by a stand, the figure showing fog emanating from the container falling toward a surface under the stand.

Regardless of whether a light diffuser 110 is provided, the container 100 may be supported by a stand 120 (as shown in FIG. 5) thereby maintaining the container 100 above a surface 122. In this embodiment, when the fog is emitted by the liquid 50 in the container 100, it may fall to the surface 122, provided the fog is more dense than the ambient air surrounding the container 100.

Figure 8:
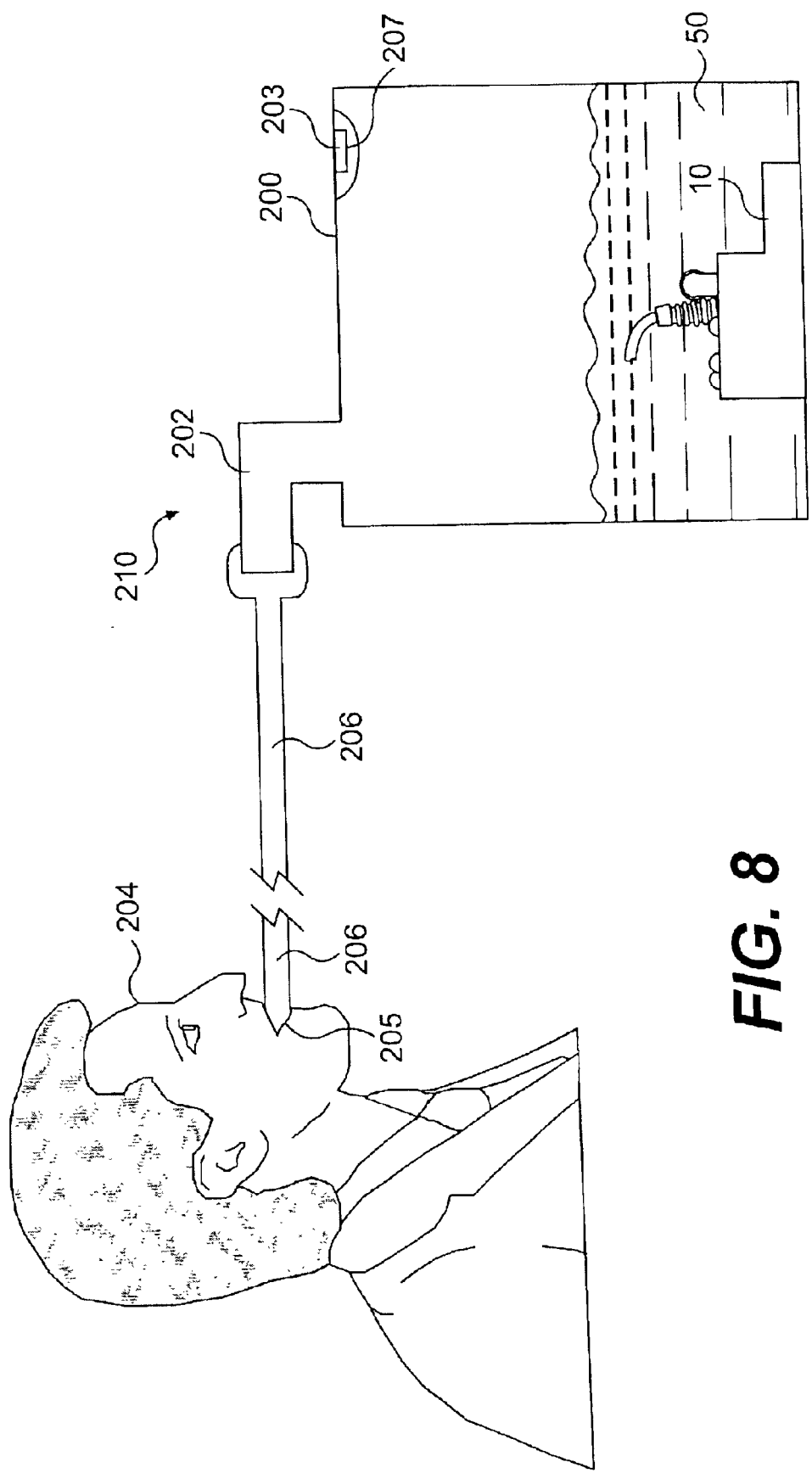
FIG. 8 is a depiction of an alternate embodiment fog generator in which an ultrasound transducer and liquid are contained within a dispenser which has an outlet for directing fog to a patient through a conduit.

FIG. 8 is a depiction of an alternate embodiment fog generator 210 in a housing 10 (as previously described) and liquid 50 are contained within a dispenser 200. The dispenser 200 has an outlet 202 for directing fog to a patient 204 through a conduit 206, the conduit 206 preferably being formed of a flexible hose made of, for example, plastic or rubber. Essentially, this embodiment of the fog generator 210 works in the same manner as the previously described embodiments. However, the fog produced thereby is channeled through the outlet 202 and into a proximal end of the conduit 206. To prevent condensation of the fog in the conduit 206, the length of the conduit 206 is preferably less than about 6". In addition, to prevent a vacuum from being creating in the dispenser 200, an air inlet 203 may be provided. Further, to prevent fog from inadvertently leaving the dispenser 200 through the inlet 203, an air filter 207 may be provided which substantially covers the inlet 203.

If the patient 204 maintains a distal end of the conduit 206 in his mouth 205, the fog may be inhaled into one or both of the patient's lungs. If the liquid 50 is a pharmaceutical, the fog thereof which is inhaled can be quickly transported to the blood of the patient via the capillaries in the lungs. In addition, if the patient suffers from asthma or other lung condition, the delivery to the lungs of the pharmaceutical in the form of the fog can provide quick treatment for such condition.

Although the aforementioned describes embodiments of the invention, the invention is not so restricted. It will be apparent to those skilled in the art that various modifications and variations can be made to the disclosed preferred embodiments of the present invention without departing from the scope or spirit of the invention. Accordingly, it should be understood that the apparatus and method described herein are illustrative only and are not limiting upon the scope of the invention, which is indicated by the following claims.

What is claimed is:

1. A housing for an ultrasonic fog generator, the housing comprising:

a transducer adapted to vibrate ultrasonically, wherein when the housing is positioned in a source comprising a liquid and when the transducer vibrates ultrasonically, the housing is adapted to create a fog from the liquid in the source, the fog emanating from the liquid source; and a visually appealing display adapted to alter an appearance of the fog, the visually appealing display comprising:

a stand adapted to support the housing; and at least two lights adapted to radiate light of at least two different colors, wherein the stand maintains the housing and the liquid source above a surface, and wherein the fog is adapted to fall toward the surface after emanating from the liquid source.

2. The housing according to claim 1, wherein the housing is adapted to be hand-held.

3. The housing according to claim 1, wherein the liquid is water.

4. The housing according to claim 1, wherein the fog is in the form of a mist.

5. The housing according to claim 1, further comprising: a sensor.

6. The housing according to claim 5, wherein the sensor is adapted to monitor a property of the liquid contacting the housing, and wherein a current control system is adapted to stop vibration of the transducer in response to the monitored property.

7. The housing according to claim 1, wherein the colors which the lights are adapted to radiate are variable.

8. The housing according to claim 1, wherein the visual display further comprises a light diffuser through which the at least two colors of light pass.

9. The housing according to claim 1, wherein the transducer is adapted to vibrate at between about 1.6 MHz and about 1.8 MHz.

10. The housing according to claim 1, wherein the transducer is adapted to vibrate at about 1.7 MHz.

11. The housing according to claim 1, wherein the liquid comprises a fragrance that is dispersed in the fog.

12. A method for adding at least one fragrance to ambient air in a room, the method comprising the steps of:

providing a housing according to claim 1, the housing further comprising the at least one fragrance, wherein each of the at least one fragrance is in a substantially liquid form;

vibrating ultrasonically the at least one fragrance with the transducer, to create a fog of the at least one fragrance; and emanating the fog formed of the at least one fragrance into the ambient air.

13. The method according to claim 12, wherein the fragrance is dissolved in a liquid solvent.

14. The method according to claim 13, further comprising the step of:

monitoring a property of the at least one fragrance and the liquid solvent in the housing with a sensor.

15. The method according to claim 14, further comprising the step of:

stopping the vibrating of the transducer if property of the at least one fragrance and the liquid solvent in the housing, as measured by the sensor, is outside a predetermined range for the property.

16. The method according to claim 12, wherein the step of vibrating ultrasonically the at least one fragrance with the transducer comprises:

vibrating the transducer at between about 1.6 MHz and about 1.8 MHz.

17. The method according to claim 16, wherein the step of vibrating ultrasonically the at least one fragrance with the transducer comprises:

vibrating the transducer at about 1.7 MHz.

* * * * *